United States Patent [19]

O'Neil

[11] 4,260,378
[45] Apr. 7, 1981

[54] SELF STABILIZING INTRA-ORAL SALIVA EVACUATOR

[76] Inventor: Robert J. O'Neil, 2995 McGill St., Vancouver, B.C., Canada, V5K 1H8

[21] Appl. No.: 44,470

[22] Filed: Jun. 1, 1979

[51] Int. Cl.³ .............................................. A61C 17/04
[52] U.S. Cl. ........................................ 433/93; 433/96
[58] Field of Search ...................... 433/91, 92, 93, 94, 433/95; 128/12, 13, 14

[56] References Cited

U.S. PATENT DOCUMENTS

| | | | |
|---|---|---|---|
| 1,401,646 | 12/1921 | Ronn | 433/93 |
| 3,396,468 | 8/1968 | Dayhoff | 433/93 |

Primary Examiner—Robert Peshock
Attorney, Agent, or Firm—Sellers & Brace

[57] ABSTRACT

A self-stabilizing intra-oral saliva evacuator insertable astride the mandibular and maxillary arches to hold the oral cavity open and to maintain the upper and lower molars dry and isolated from contact with the lingual and buccal tissues so long as the evacuator is in place. The semi resilient tempered main body is supported solely by the teeth and a major portion thereof is embraced by flexible tubing connected to evacuating facilities and is provided with strategically located orifices to remove saliva and maintain a particularly copious flow of ambient drying air over the adjacent dental surfaces. The two-part main body, though a permanent assembly, can be readily adjusted to accommodate a range of different oral cavity configurations.

23 Claims, 5 Drawing Figures

SELF STABILIZING INTRA-ORAL SALIVA EVACUATOR

This invention relates to dental appliances, and more particularly to an improved and unique self-stabilizing intra-oral saliva evacuator functioning to maintain the oral cavity widely open while maintaining the teeth along at least one side of the cavity thoroughly dry and free of saliva.

BACKGROUND OF THE INVENTION

The patient's nervous tension and apprehension aggravates and augments the flow of saliva and seriously hampers the performance of dental services. Cleaning, coating, prophylactic and other dental work performed on the teeth can also cause considerable blood and saliva flow and these fluids along with cuttings and other foreign matter must be removed. A wide variety of saliva and foreign matter ejectors have been proposed to alleviate these problems. Typical constructions are disclosed in the following U.S. Pat. Nos.: 342,042 Rowney; 2,028,381 Dewitt; 2,830,371 Dahl; 2,844,873 Bober; 24,693 Thompson Re-issue; 2,950,533 Sommerstein; 3,078,578 White; 3,396,468 Dayhoff. Each of the foregoing devices as well as other commercial variants available to the dental profession and coming to my attention are subject to serious deficiencies and shortcomings. For example, many of these devices, such as those shown by Rowney and Sommerstein, are supported merely by gravity in the oral cavity or must be held or manipulated by the patient, the dentist or his assistant. In recognition of these shortcomings proposals have been made for ejectors equipped with means engagable with the patient's jaw to hold the ejector seated against the bottom of the oral cavity. Examples of devices of this type are shown by White, Dewitt, Dahl and Bober. Not only do such devices impose objectionable pressure on oral cavity tissues and the underside of his chin but they increase the patient's discomfort and lack provision for preventing closure of the mouth. They have inadequate and unacceptable provision for keeping selected denture surfaces dry and uncontaminated by saliva, blood, detritus and moisture from the patient's breath. Dayhoff and Thompson show saliva ejectors incorporating some means for holding the oral cavity open. Dayhoff's ejector is formed entirely of semi-flexible plastic tubing straddling the upper and lower arches and supports a flexible elastic sheet or dam having cut outs through which the teeth project and includes a vertical wall to isolate the tongue. This contruction is bulky, difficult and time consuming to install and uncomfortable. Thompson proposes a jaw spacer accessory which can be inserted in orifices of a perforated tubular saliva ejector to hold the latter pressed against the floor of the oral cavity. It lacks lingual guard protection and any provision for draining saliva from the parotid salivary duct and the upper molars.

SUMMARY OF THE INVENTION

The foregoing and many other shortcomings and disadvantages of prior practice and teachings relating to intra-oral evacuators are avoided by this invention. My evacuator typically comprises a semi-resilient main frame preferably made in two relatively adjustable parts. Major portions of this frame are enclosed in loose fitting flexible tubing provided with a multiplicity of strategically positioned inlet orifices. The frame includes U-shaped lingual and buccal loops the legs of which are inter-connected by bridging members straddling the upper and lower alveolar ridges and cooperating with the loops to maintain the mouth firmly and widely open. Only the bridging members have pressure contact with any part of the oral cavity and this contact is solely with the upper and lower cuspids and the adjacent molars. The lower leg of the buccal loop is readily adjustable in length and frictionally retained in a selected adjusted position thereby to accommodate the evacuator to different oral cavity sizes and conditions and so as to provide unobstructed access to all molar surfaces. Additionally and importantly, both the internal diameter of the evacuator tubing and the evacuator ports preferably are sufficiently large as to utilize to maximum advantage the air flow capabilities of modern suction facilities. In consequence a sufficient flow of relatively dry breath-free ambient air is maintained over the teeth undergoing treatment to prevent the deposit of moisture thereon from the patient's breath. Adjustment of the buccal loop also aids materially in positioning a critically important saliva orifice adjacent the outlet end of the parotid salivary duct. The lingual loop includes a lingual guard and its upper portion is also constructed and positioned to cooperate with this guard not only in isolating the maxillary molars from contact by the tongue but in strongly resisting movement of the jaws toward closure. Normally only one evacuator is used at a time but on other occasions a pair of evacuators may be inserted on respective sides of the oral cavity. These evacuators are identical except that one is designed for use on the right and the other on the left side of the oral cavity.

Accordingly it is a primary object of this invention to provide a unique self-stabilizing saliva evacuator.

Another object of the invention is the provision of an intra-oral evacuator operating to maintain the oral cavity firmly open with bearing contact only with dental surfaces.

Another object of the invention is the provision of an intra-oral evacuator for maintaining the upper and lower molars not only free of saliva and completely dry but isolated from the lingual and buccal tissue surfaces.

Another object of the invention is the provision of an intra-oral evacuator having a semi-resilient metallic frame embraced in major by loose fitting perforated tubing connectable to evacuating facilities.

Another object of the invention is the provision of an intra-oral evacuator having a metallic tempered main frame readily adjustable to accommodate a range of oral cavity configurations and sizes.

Another object of the invention is the provision of an intra-oral evacuator avoiding the need for elastic dams, absorbent rolls, packings and pressure contact with tissue.

Another object of the invention is the provision of an intra-oral evacuator capable of maintaining a copious flow of ambient substantially breath-free air over teeth undergoing treatment in excess of that serving to remove saliva and detritus thereby safeguarding against the deposit of moisture on those teeth from the patient's breath.

Another object of the invention is the provision of an intra-oral evacuator providing for highly successful prophylactic treatments, or application of bonding coatings to dental surfaces, and other procedures and treatments wherein dryness of the dental surfaces is a crucially important prerequisite.

These and other more specific objects will appear upon reading the following specification and claims and upon considering in connection therewith the attached drawing to which they relate.

Referring now to the drawing in which a preferred embodiment of the invention is illustrated;

Figure 1:
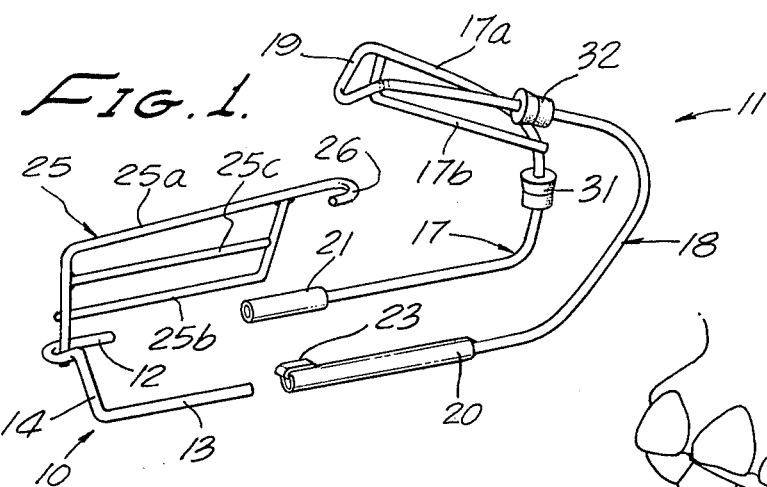
FIG. 1 is an exploded perspective view of the main frame of the evacuator.

Referring initially and more particularly to FIG. 1, it will be understood that the main frame of the evacuator, as there shown, is made in two parts designated generally 10 and 11. Each part is made primarily of tempered resilient material, such as stainless steel wire. Part 10 is generally U-shaped and includes a short leg 12 and a longer leg 13 inter-connected by an upwardly humped bridging member 14. The second part 11 of the main frame comprises two U-shaped loops 17 and 18 having the free ends of their upper legs interconnected by a downwardly humped bridging member 19. The free ends of the other two legs of loop 17 and 18 terminate in a relatively long tube 20 and a shorter tube 21 having a sliding frictional fit with legs 12 and 13 of part 10. The open ends of tubes 20 and 21 are positioned generally in the same transverse plane. This facilitates the insertion of leg 13 into tube 20 prior to the insertion of leg 12 into tube 21, it being understood that normally parts 10 and 11 are telescopically assembled to one another in a manner and for purposes which will be explained more fully presently. The open end of at least tube 20 is provided with a reversely bent tang 23 the purpose and functions of which will be explained below.

Part 10 of the main frame also includes a lingual guard 25 here shown as comprising a pair of L-shaped elements 25a, 25b having their upright legs interconnected by an element 25c and suitably silver soldered together. Guard 25 is spot welded or otherwise firmly secured to part 10 at the junction of its leg 12 with bridging member 14. The remote end of guard 25 has a loop 26 which, upon assembly, is snugly closed about the bight portion of the lingual loop 17. The upper leg 17a of loop 17 is held against flexure by an L-shaped guard element 17b having its legs lying generally in a vertical plane when the evacuator is in use. The shorter leg is secured to upper leg 17a adjacent bridging member 19 and its longer leg is secured to the bight portion of loop 17 somewhat above loop 26 of guard 25. It will therefore be apparent that guard members 17b and 25 cooperate in severely limiting the flexibility of lingual main body loop 17.

Figure 2:
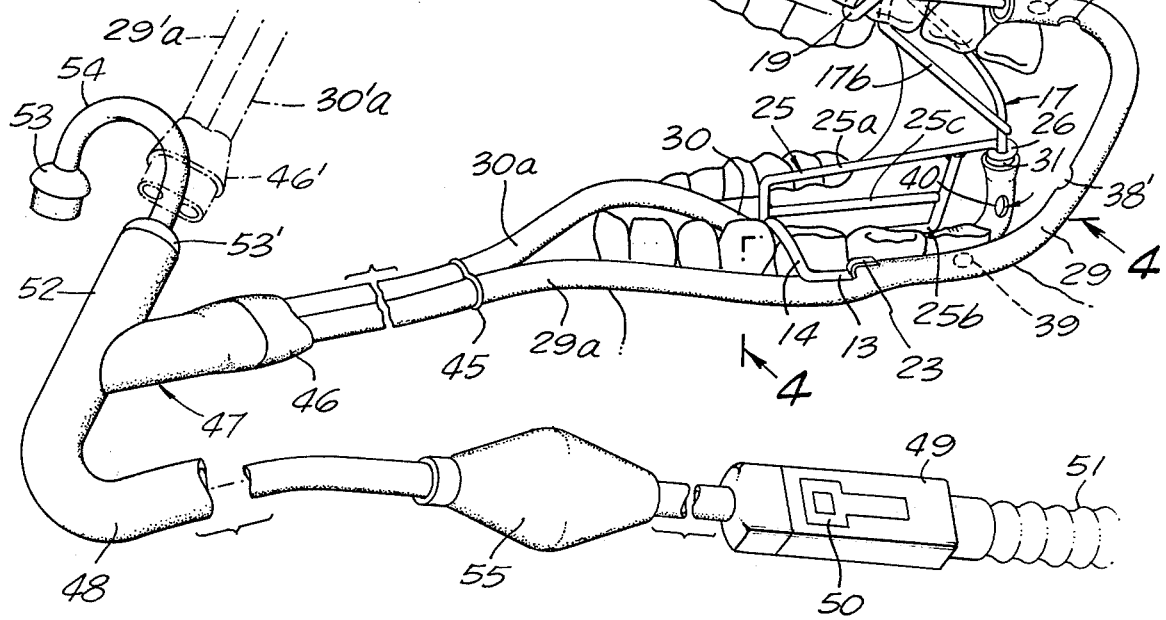
FIG. 2 is a perspective view of the evacuator supported on the alveolar ridges on the left side of the oral cavity as viewed in side elevation.
Figure 3:
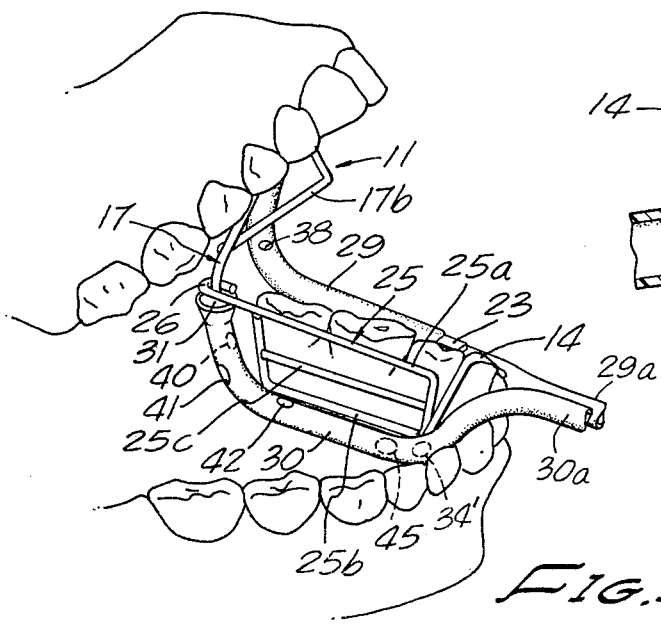
FIG. 3 is a view similar to FIG. 2, as viewed from the right side of the oral cavity.

Referring now more particularly to FIGS. 2 and 3, it will be observed that the lower leg and bight portion of the lingual loop 17 and the major portion of the buccal loop 18 are embraced by flexible, loose-fitting separate elastomeric tubes 29 and 30. The internal diameter of each of these tubes is substantially larger than the main frame members 17 and 18 and permit copious and free flow of air, saliva and detritus to a point of disposal. The upper end of tube 29 has a fluid tight telescopic fit over a plug 32 soldered or otherwise fixed to loop 18. Likewise the end of tube 30 has a similar snug fit over plug 31.

Figure 4:
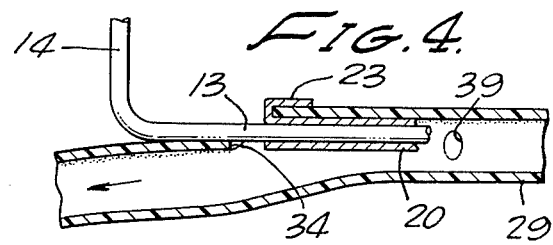
FIG. 4 is a fragmentary cross sectional view on an enlarged scale taken along line 4—4 on FIG. 2.

Referring now to FIGS. 2 and 4, it is pointed out that tubing 29 is provided with an orifice 34 closely adjacent tang 23 integral with the outer end of tube 20. Tubing 29 is telescoped over buccal loop 18 while part 10 of the main frame is separated from part 11 until its foremost end is seated on plug 32 and may be bonded thereto if this is desired. Normally, however, no bonding agent is required. Tang 23 is inserted through opening 34 and astride the rim edge thereof as shown in FIG. 4. It will now be clear that tubing 29 is held securely in place on loop 18 and that opening 34 is properly positioned to receive leg 13 of the main frame part 10. A similar opening 34' in tubing 30 (FIG. 3) is aligned with the entrance end of tube 21 (FIG. 1) in position to receive leg 12 of main frame part 10.

The portions of tubing 29 and 30 embracing the legs of loops 17 and 18 are provided with a series of orifices suitably disposed for the most effectual induction of the fluids and detritus. Thus the portion of tubing 29 embracing the buccal loop 18 is provided with at least 4 orifices 36, 37, 38 and 39, and may include additional ones particularly along the lower leg of the loop. Orifice 36 faces inwardly and orifice 37 faces generally downwardly and these provide a copious induction flow of air past the upper molars and also induct saliva discharging from the end of the parotid salivary gland duct the outlet of which is located closely adjacent the base of the upper rear molar in the area of orifices 36 and 37 as shown in FIG. 2. Orifices 38 and 39 are suitably disposed for inducting a flow of air and saliva in their vicinity.

Tubing 30 embracing the lingual loop 17 is provided with at least four orifices and may include others if desired. Orifice 40 faces inwardly and assures a copious flow of air past the lower molars. Orifices 41, 42 and 43 face outwardly and in some instances downwardly as is best indicated in FIG. 3 and function to provide a flow of drying air over dental surfaces and to remove saliva, wash water and detritus from the oral cavity floor.

Modern dental suction equipment has high air flow capabilities and tubing 29, 30 and the ports thereof are preferably sized to utilize this high flow capability to maximum advantage. As will be recognized from the showing in FIGS. 2–5, the high volume air flow is provided essentially from dry ambient room air which is substantially free of moisture commonly present in the patient's breath. This copious flow of dry air shields the teeth under treatment from contact with the patient's breath in a highly effective manner thereby resolving a problem which has long plagued the dental profession and heretofore resolved only by resort to costly and time consuming rubber dam expedients.

The outer ends of tubing 29a and 30a may be secured together as by banding 45 and connected to a male coupling 46 having a snug frictional fit within one of the branches of a tubular Y fitting 47 of flexible elastomeric material. The long stem 48 of the junction fitting includes a manually operable valve 49 of conventional construction having an operating button 50 for regulating the suction pressure and for cutting off flow should this be desirable. Valve 49 is connected by flexible hose 51 to suction creating means equipped with a suitable liquid and detritus separator.

The other branch 52 of Y fitting 47 may be connected to a second evacuator device differing from that shown and described in FIGS. 1, 2 and 3 only in being designed for mounting on the right rather than the left side of the oral cavity. Since this evacuator is otherwise identical with that described, it has not been shown except that its presence is indicated by the dot and dash line showing of its fluid flow tubing 29'a and 30'a along with its male connector 46'. This connector is insertable in branch 52 of the Y connector 47. When the unshown right evacuator is not in use the inlet of branch 52 is closed by one of a pair of identical plugs 53, 53'. These plugs are interconnected by a flexible loop 54. Plugs 53 and 53' are inserted in their respective branches of the Y fitting to prevent the entry of air when only one evacuator is in use. Suction line 48 also preferably includes an enlargement 55 located adjacent valve 49 and serving as a convenient manipulating handle for the evacuating tubing.

The mode of use of the evacuator device will be quite apparent from the foregoing detailed description of its components. Assuming that the left hand evacuator is assembled as shown in FIG. 2, it is a simple operation to insert the device in the oral cavity. The legs of the loops 17 and 18, but predominantly 18 are compressed toward one another while being inserted astride the mandibular and maxillary ridges on the left hand side of the oral cavity and then released to seat the bridging members 14 and 19 firmly in the valley between a related pair of cuspids and forward molars. The bridging members seat very firmly and securely in these valleys, the entire load forces being imparted to these pairs of teeth and sustained by the respective alveolar ridges. To be noted in particular is the fact that all other portions of a properly inserted evacuator are out of contact with tissues including the floor and roof of the oral cavity.

Adjustment of the buccal loop is frequently desirable in order that the juxtaposed surfaces of the molars will be unobstructed and freely accessible for treatment and all other dental operations. Adjustment is accomplished simply by placing the index finger against bridge 14 while using the fingers of the other hand to shift loop 18 forwardly or rearwardly along leg 13 of bridging member 14. Owing to the close sliding fit between leg 13 and tube 20 of loop 18, these parts remain reliably and firmly in any of a wide number of adjusted positions. Thus if tube 20 is shifted rearwardly along leg 13 thereby lengthening the lower leg of loop 18, such lengthening serves to pivot loop 18 counter-clockwise thereby tilting the upper leg upwardly about the pivot point provided by bridging member 19 thereby enhancing access to the upper molars and/or the position of orifices 36 and 37. When working on the lower molars the evacuator may be readjusted and pivoted clockwise to provide greater accessibility and less obstruction while working on the lower molars. Adjustment of leg 13 within tube 20 also greatly aids proper positioning of the various orifices for most effective evacuating of fluids.

The inner loop 17 of the evacuator is not adjustable in length but is held rigidly in place by the upper and lower lingual guards 17b and 25. Additionally and importantly these two guard units severely limit the flexibility of the inner U-shaped main frame loop 17 with the result that the patient cannot close the mouth while the evacuator is installed as shown in FIGS. 2 and 3.

Figure 5:
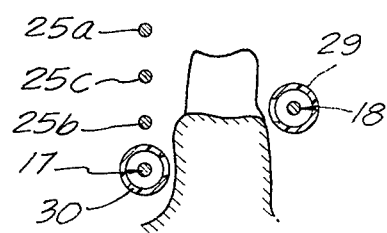
FIG. 5 is a fragmentary vertical sectional view taken through the mandibular arch and related portions of the invention evacuator in a typical operating position.

As will be observed from FIGS. 2 and 3 and particularly FIG. 5, all surfaces of the molars are fully exposed and unobstructed. Moreover the various fluid inlet orifices are positioned to remove any saliva or washing water quickly as well as to maintain a copious flow of drying air over the molars. The evacuator is firmly anchored in place and is fully self-stabilizing and self-centering and permits the technician or dentist to proceed with highly efficient and effective prophylactic and coating treatments the success of which is critically dependent upon maintaining the treated surfaces absolutely dry and free of risk of contact with the tongue or buccal tissues. Moreover, the patient's mouth is held open firmly and comfortably and free of pressure on the gums, the floor or the roof of the oral cavity. Likewise the patient may swallow naturally and comfortably.

So long as the suction control valve 50 remains open large volumes of ambient relatively dry air are drawn into the oral cavity, and into the numerous inlet orifices 36 to 43. This relatively dry and breath-free air quickly dries the teeth and maintains them dry, a condition so critically important to many dental operations and treatments.

While the particular self stabilizing intra-oral saliva evacuator herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

I claim:

1. A self-stabilizing intra-oral evacuator for evacuating saliva from aligned sets of upper and lower molars and for passing air thereover to maintain the same dry while undergoing treatment or dental work comprising:

a pair of spaced-apart semi-resilient U-shaped metallic members, the free ends of the legs of said pair of metallic members being interconnected by metallic bridging portions adapted to rest astride a non-tissue portion of a respective one of the mandibular and maxillary arches in a self-stabilizing manner along one side of the oral cavity and which bridging members cooperate with said semi-resilient U-shaped members in holding said arches open and against closing by the patient so long as installed; and flexible tubing loosely assembled over a major portion of said U-shaped metallic members, said tubing having a series of saliva and air inlet openings disposed, in part, adjacent the root ends and, in part, adjacent the crowns of juxtaposed ones of said molars and adapted to be connected to evacuating means while said appliance is installed in an oral cavity.

2. An intra-oral evacuator as defined in claim 1 characterized in that the legs of said U-shaped members are essentially free of pressure contact with tissue of the oral cavity when installed and the legs of each U-shaped member tending to spread apart in the general plane thereof and cooperating with said bridging portions to maintain said mandibular and maxillary arches opened away from one another.

3. An intra-oral evacuator as defined in claim 1 characterized in that said U-shaped members are so disposed and shaped when installed in the oral cavity that the surfaces of the molars therebetween are out of contact with the legs of said U-shaped members and accessible for inspection, treatment and repair operations.

4. An intra-oral evacuator as defined in claim 1 characterized in that the legs of said U-shaped members are out of pressure contact with tissues adjacent molars of the mandibular and maxillary arches when said evacuator is properly installed in the oral cavity.

5. An intra-oral evacuator as defined in claim 1 characterized in that one leg of one of said U-shaped member is adjustable lengthwise thereof.

6. An intra-oral evacuator as defined in claim 5 characterized in that said one leg includes a tubular portion having a snug telescopic fit with another part of said one U-shaped member and effective to retain a selected adjustment until deliberately shifted to a different adjustment.

7. An intra-oral evacuator as defined in claim 5 characterized in that said one adjustable leg is located adjacent the buccal side of the mandibular arch when said appliance is installed in the oral cavity.

8. An intra-oral evacuator as defined in claim 1 characterized in that the U-shaped member on the lingual side of said evacuator includes a lingual guard extending along and spaced inwardly from the adjacent mandibular molars to prevent the tongue from contacting or wetting the inner surfaces of these molars.

9. An intra-oral evacuator as defined in claim 1 characterized in that both legs of the U-shaped member on the lingual side thereof are equipped with lingual guard means extending along and spaced inwardly from a respective group of molars to prevent the tongue from contacting the surfaces thereof.

10. A self-stabilizing intra-oral evacuator adapted to bear against and to be installed astride the mandibular and maxillary arches to urge and hold the same resiliently apart and against closing by the patient while aspirating air and saliva from the upper and lower molars during treatment, said evacuator comprising:
a semi-resilient main body having a pair of U-shaped metallic members lying generally in spaced apart planes with each pair of adjacent legs interconnected by metallic bridging means each adapted to rest astride and to be supported by a non-tissue portion of a respective mandibular and maxillary arch on one side of the oral cavity and cooperating with the resiliency of said main body to urge and hold those arches opened widely apart and said main body firmly in place in an oral cavity and with said legs spaced away from the adjacent sides of the juxtaposed molars; and
flexible tubing telescoped loosely over a plurality of said legs, said tubing having a plurality of perforations distributed along said legs for the inflow of saliva and air when said tubing is connected to evacuating means, and said perforations being disposed to remove saliva from about said molars and maintain a flow of air therepast.

11. An intra-oral evacuator as defined in claim 10 characterized in the provision of lingual guard means along and cooperating with the leg of said main body adjacent the inner side of the mandibular arch to prevent the tongue from contacting the mandibular molars.

12. An intra-oral evacuator as defined in claim 10 characterized in that said bridging means adapted to rest astride said mandibular arch comprises a U-shaped member the legs of which have a telescopic fit with the free ends of the legs of said pair of main body members.

13. An intra-oral evacuator as defined in claim 12 characterized in that one of said pair of telescoping legs is adjustable lengthwise of one another to different stable positions.

14. An intra-oral evacuator as defined in claim 12 characterized in the provision of lingual guard means extending along and cooperating with the leg of said main body adjacent the inner side of the mandibular arch to prevent the tongue from contacting the mandibular molars.

15. An intra-oral evacuator as defined in claim 10 characterized in that one of said U-shaped members includes means for limiting flexure movement of the legs thereof toward one another whereby said main body is effective to hold the mandibular and maxillary arches widely and firmly open.

16. An intra-oral evacuator as defined in claim 15 characterized in that said means for limiting flexure movement of said legs is mounted on the U-shaped member located on the lingual side of the molars.

17. An intra-oral evacuator as defined in claim 12 characterized in the provision of tang means on a leg of one of said first mentioned U-shaped members extending into an opening in the wall of said tubing and effective to hold said tubing in assembled position when said bridging means is withdrawn from telescopic assembly to said first mentioned U-shaped members.

18. A pair of intra-oral evacuators as defined in claim 10 and differing in that each is shaped for assembly astride a respective side only of the mandibular and maxillary arches, and said flexible tubing including coupling means having provision for coupling either one or both of said appliances to common evacuating means.

19. A self-stabilizing intra-oral evacuator for holding the mandibular and maxillary arches widely open and the molars affixed to said arches dry and free of saliva, and evacuator comprising:
a resilient metallic main body including a U-shaped lingual loop and a U-shaped buccal loop held in spaced apart, side by side relation by a first integral bridging portion between the ends of one pair of legs of said loops, said bridging portion being adapted to rest astride and against teeth of the maxillary arch, a second bridging portion interconnecting the other pair of said loops and adapted to rest astride and against teeth of the mandibular arch and adapted to cooperate with said U-shaped loops and said first bridging portion to hold said arches widely open and against closing by the patient so long as installed therebetween and to hold said evacuator firmly anchored in situ; and
flexible perforated tubing loosely telescoped over major portions of said U-shaped loops and adapted to be connected to a source of evacuation thereby to withdraw saliva and maintain a flow of air from the region of the juxtaposed mandibular and maxillary molars.

20. An intra-oral evacuator as defined in claim 19 characterized in that said first and second bridging portions of said main body are sized to rest between an adjacent pair of teeth to anchor said appliance against movement lengthwise of said arches.

21. An intra-oral evacuator as defined in claim 20 characterized in that said second bridging portion is generally U-shaped and in that one leg thereof is frictionally and telescopically shiftable lengthwise of the legs of said buccal loop thereby to vary the position of the portion of said buccal loop adjacent the rearmost molar on said maxillary arch.

22. An intra-oral evacuator as defined in claim 21 characterized in the provision of means for limiting flexure movement of the U-shaped leg on the lingual side of said evacuator.

23. An intra-oral evacuator as defined in claim 19 characterized in that said tubing and the perforations thereof are sized to accommodate a high volume flow of room air into the patient's mouth and over the teeth straddled by said evacuator thereby greatly minimizing the possibility of moisture from the patients breath contacting teeth undergoing treatment.

* * * * *